US00PP12530P2

(12) United States Plant Patent
Vandenberg

(10) Patent No.: US PP12,530 P2
(45) Date of Patent: Apr. 9, 2002

(54) CHRYSANTHEMUM PLANT NAMED 'REGAL YOLANSING'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/594,762

(22) Filed: Jun. 16, 2000

(51) Int. Cl.[7] ..... A01H 5/00
(52) U.S. Cl. ..... Plt./287
(58) Field of Search ..... Plt./287, 292

(56) References Cited

U.S. PATENT DOCUMENTS 4,616,099 A * 10/1986 Sparkes ..... 47/58

OTHER PUBLICATIONS

Shukla, et al., 1993, "Mutation studies on early and late varieties of garden chrysanthemums", J. Nuclear Agric. Biol., 22(3–4): 138–142.*
Broertjes, et al., 1980, "A mutant of a mutant of a . . . Irradiation of progressive radiation induced mutants in a mutation breeding programme with *Chrysanthemum morifolium,*" Euphytica 29: 525–530.*
Gosling, ed., 1979, "The Chrysanthemum Manual—6$^{th}$ edition", The National Chrysanthemum Society, London, Essex Telegraph Press, Ltd., pp. 329–336.*
Broetjes, et al., 1978, "Application of Mutation Breeding Methods in the Improvement of Vegetatively Propagated Crops", Elsevier Sci. Pub. Co., New York, pp. 162–175.*
Searle, et al., 1968, "Chrysanthemums the Year Round", Blanford Press, London, pp. 27–29, 320–327.*
Chan, 1966, Chrysanthemum and rose mutations induced by x–rays, Am Soc. Hort. Sci. Proc., pp. 613–620.*
Broertjes, 1966, "Mutation breeding of chrysanthemums", Euphytica, 15:156–162.*
Dowrick, et al., 1966, "The induction of mutations in chrysanthemum using X–and gamma radiation", Euphytica, 15:204–210.*
UPOV–ROM, 2001/03, Plant Variety Database, GTI Jouve Retrieval Software, citation for 'Regal Yolansing'.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Regal Yolansing', characterized by its upright and uniformly mounded plant habit; vigorous growth habit; uniform flowering response; early flowering, eight-week response time; larger decorative-type inflorescences that are about 10.1 cm in diameter; purple-colored ray florets; and good postproduction longevity with inflorescences maintaining good substance and color for about three weeks in an interior environment.

1 Drawing Sheet

BACKGROUND OF THE INVENTION

The present Invention relates to a new and distinct cultivar of Chrysanthemum plant, botanically known as *Dendranthema grandiflora* and hereinafter referred to by the cultivar name Regal Yolansing.

The new Chrysanthemum is a product of a mutation induction breeding program conducted by the Inventor in Fort Myers, Fla., and Salinas, Calif. The objective of the program is to create new Chrysanthemum cultivars with desirable inflorescence form and floret colors and good postproduction longevity.

The new Chrysanthemum originated by exposing unrooted cuttings of the Chrysanthemum cultivar Yolansing, disclosed in U.S. Plant Pat. No. 11,209, to X-ray radiation in December, 1996, in Fort Myers, Fla. Following the radiation treatment, the cuttings were rooted and terminal apices were removed (pinched) three times to promote lateral branch development. After lateral branches form the third pinch reached sufficient size, terminal cuttings were harvested, planted and flowered in a controlled environment in Salinas, Calf. The new Chrysanthemum was discovered and selected by the Inventor as a single flowering plant within this population in July, 1997. The selection of this plant was based on its desirable inflorescence form and ray floret color.

Asexual reproduction of the new Chrysanthemum by vegetative tip cuttings was first conducted in Salinas, Calif. in October, 1997. Asexual reproduction by cuttings has shown that the unique features this new Chrysanthemum are stable and reproduced true to type in successive generations.

SUMMARY OF THE INVENTION

The cultivar Regal Yolansing has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Regal Yolansing'. These characteristics in combination distinguish 'Regal Yolansing' as a new and distinct Chrysanthemum:

1. Upright and uniformly mounded plant habit.
2. Vigorous growth habit.
3. Uniform flowering response.
4. Early flowering, eight-week response time.
5. Large decorative-type inflorescences that are about 10.1 cm. in diameter.
6. Purple-colored ray florests.

7. Good postproduction longevity with inflorescences maintaining good substance and color for about three weeks in an interior environment.

Plants of the new Chrysanthemum differ from plants of the parent cultivar Yolansing in the following characteristics:

1. Plants of the new Chrysanthemum are slightly less vigorous and slightly shorter than plants of the cultivar Yolansing.

2. Ray floret color of plants of the new Chrysanthemum is darker purple than ray floret color of plants of the cultivar Yolansing.

3. Plants of the new Chrysanthemum flower about one to three days later than plants of the cultivar Yolansing.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top for the sheet comprises at top perspective view of a typical flowering plant of 'Regal Yolansing'.

The photograph at the bottom of the sheet comprises a close-up view of typical inflorescences of the cultivar Regal Yolansing.

DETAILED BOTANICAL DESCRIPTION

In the following description, color references are made to The Royal Horticultural Society Colour Chart except where general terms of ordinary dictionary significance are used. The following observations and measurements describe plants grown and flowered during the Spring in Salinas, Calif. and Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbud-types. Measurements and numerical values represent averages of typical flowering plants.

Botanical classification: *Dendranthema grandiflora* cultivar Regal Yolansing.

Commercial classification: Decorative-type potted Chrysanthemum.

Parentage: Induced mutation of *Dendranthem grandiflora* cultivar Yolansing, disclosed in U.S. Plant Pat. No. 11,209.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative-type potted Chrysanthemum typically grown as a disbud-type. Inverted triangle; stems mostly upright; uniformly mounded appearance. About four lateral branches develop after removal of terminal apex (pinching); full and dense plants. Vigorous growth habit.

*Plant height.*—About 26 cm.

*Plant width.*—About 34 cm.

*Lateral branches.*—Length: About 18 cm. Diameter: About 4 mm. Internode length: About 2.3 cm. Strength: Strong. Texture: Pubescent. Color: 144A.

*Foliage description.*—Arrangement: Alternate. Length: About 5.9 cm. Width: About 5.3 cm. Apex: Cuspidate. Base: Attenuate. Margin: Palmately lobed, sinuses between lateral lobes mostly divergent. Texture: Upper and lower surfaces with very fine pubescence; veins prominent on lower surface. Color: Young foliage upper surface: Darker than 147A. Young foliage lower surface: Close to 147B. Mature foliage upper surface: 147A. Mature foliage lower surface: 147B. Venation upper surface: 147A to 147B. Venation lower surface: 147B. Petiole length: About 2.5 cm. Petiole diameter: About 3 mm. Petiole color: 147A and 147B.

Inflorescence description:

*Appearance.*—Decorative-type inflorescence form with elongated oblong-shaped ray florets. Inflorescences borne on terminals above foliage. Disk and ray florets arranged acropetally on a capitulum. Not fragrant.

*Flowering response.*—Under natural conditions, plants flower in the autumn/winter in the Northern Hemsiphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences maintain good color and substance for about three weeks in an interior environment.

*Quantity of inflorescencs.*—Typically grown as a disbud-type with one inflorescence per lateral stem; about four inflorescences per plant.

*Inflorescence bud.*—Height: About 7 mm. Diameter: About 8.5 mm. Color: More green than 147A.

*Inflorescence size.*—Diameter: About 10.1 cm. Depth (height): About 2.8 cm. Diameter of disc: Less than 4 mm, inconspicuous. Receptacle diameter: About 8 mm.

*Ray Florets.*—Shape: Elongated-oblong. Orientation: Initially incurved, outer rows opening to perpendicular to stem or reflexed. Aspect: Initially concave then becoming convex with development. Length: About 4.7 cm. Width: About 1.1 cm. Apex: Acute, mammilate or emarginate. Base: Attenuate; medium corolla tube. Margin: Entire. Texture: Smooth, glabrous, satiny. Number of ray florets per inflorescence: About 215. Color: When opening, upper surface: 71A to close 72A. When opening, lower surface: 73D heavily overlaid with purple, close to 71A to 72A to 72B, longitudinal streaks. Fully opened, upper surface: 71A to close to 72A to 72B; fading to 77B. Fully opened, lower surface: 73D to 75D heavily overlaid with purple, close to 71A to 72A to 72B, longitudinal streaks.

*Disc florets.*—Shape; Tubular, flared. Apex: Five-pointed. Length: About 6 mm. Width: Apex, about 1.5 mm; base, about 1 mm. Number of disc florets per inflorescence: Less than 20; inconspicuous. Color: Immature: 144A. Mature: Apex: 5A. Midsection and base: White, 155D.

*Reproductive organs.*—Androecium: Present on disc florets only. Anther color: 9A. Pollen amount: Scarce. Pollen color: 12A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Regal Yolansing', as illustrated and described.

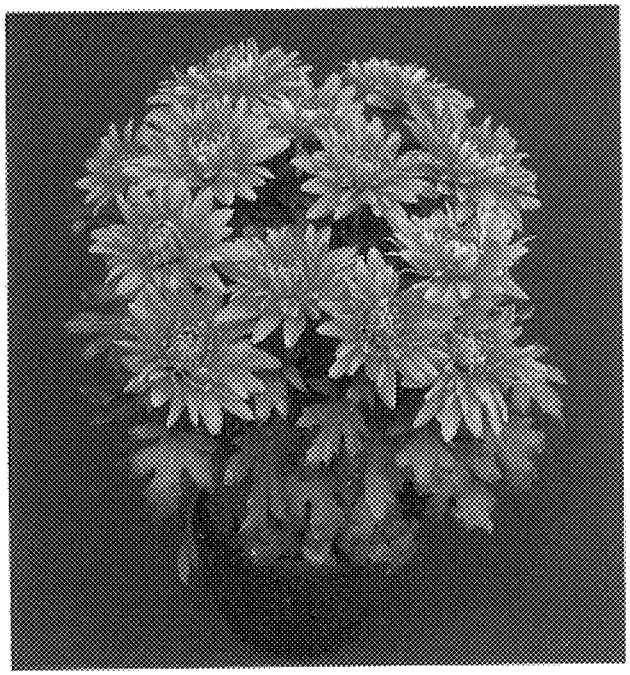
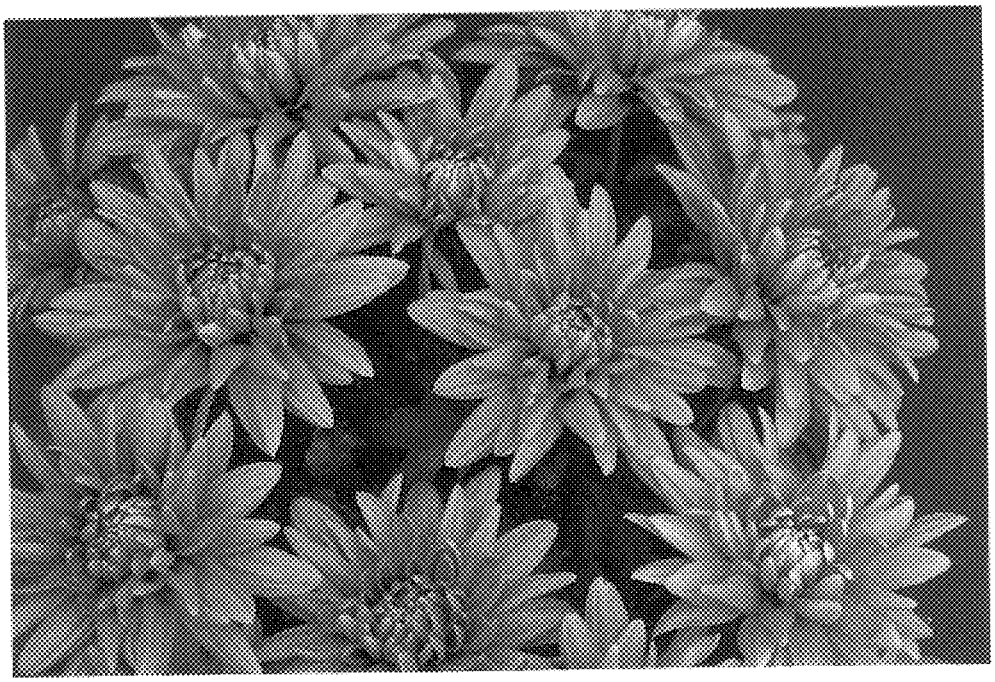

* * * * *